US00PP24429P3

(12) United States Plant Patent

Klemm et al.

(10) Patent No.: US PP24,429 P3

(45) Date of Patent: May 6, 2014

(54) *PELARGONIUM* PLANT NAMED 'KLEPZ11276'

(50) Latin Name: *Pelargonium zonale*
Varietal Denomination: KLEPZ11276

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 130 days.

(21) Appl. No.: 13/506,008

(22) Filed: Mar. 20, 2012

(65) Prior Publication Data

US 2013/0254951 P1 Sep. 26, 2013

(51) Int. Cl.
*A01H 5/00* (2006.01)

(52) U.S. Cl.
USPC ..... Plt./325; Plt./329

(58) Field of Classification Search
USPC ..... Plt./325, 329, 330
See application file for complete search history.

(56) References Cited

U.S. PATENT DOCUMENTS

| | | | | | |
|---|---|---|---|---|---|
| PP9,110 | P | * | 4/1995 | Klemm | Plt./325 |
| PP9,488 | P | * | 3/1996 | Endisch et al. | Plt./325 |
| PP11,302 | P | * | 3/2000 | Utecht | Plt./325 |
| PP14,456 | P2 | * | 1/2004 | Utecht | Plt./325 |

OTHER PUBLICATIONS

UPOV PLUTO Database 201303 No Citation for 'KLEPZ11276' Nov. 15, 2011.*

UPOV PLUTO Database 201303 QZ Citation for 'KLEPZ11276' Oct. 15, 2011.*

* cited by examiner

*Primary Examiner* — Wendy C Haas

(74) *Attorney, Agent, or Firm* — Jondle Plant Sciences Division of Swanson & Bratschun, L.L.C.

(57) ABSTRACT

A new variety of *pelargonium* named 'KLEPZ11276', particularly characterized by red-purple flowers with orange centers, good branching, medium early flowering time, healthy and strong growth habit, and leaves with zonation, is disclosed.

1 Drawing Sheet

Genus and species: *Pelargonium zonale.*
Variety denomination: 'KLEPZ11276'.

BACKGROUND OF THE NEW PLANT

The present invention comprises a new and distinct variety of *pelargonium*, botanically known as *Pelargonium zonale*, and hereinafter referred to by the variety name 'KLEPZ11276'. The new variety is the result of a controlled cross conducted in June 2006 in Nairobi, Kenya between the female *pelargonium* parent, 'KLEGANY' (U.S. Plant Pat. No. 9,110), and the male *pelargonium* parent, 'P 1101' (unpatented). A single plant selection was subsequently chosen for further evaluation and asexual propagation.

The new variety was first propagated via vegetative cuttings in September 2008 in Stuttgart, Germany and has been asexually reproduced repeatedly by vegetative cuttings in Stuttgart, Germany for approximately 6 to 8 generations. 'KLEPZ11276' has been found to retain its distinctive characteristics through successive asexual propagations via vegetative cuttings.

Plant Breeder's Rights for this variety were applied for in the following countries: Switzerland on Jul. 4, 2011, the European Union on Jul. 8, 2011, and Norway on Aug. 5, 2011. 'KLEPZ11276' has not been made publicly available or sold more than one year prior to the filing date of this application.

SUMMARY OF THE INVENTION

The following are the most outstanding and distinguishing characteristics of this new variety when grown under normal horticultural practices in a glass greenhouse in Stuttgart, Germany.

1. Red-purple flowers with orange centers, good branching;
2. Medium early flowering time;
3. Healthy and strong growth habit; and
4. Leaves with zonation.

DESCRIPTION OF THE PHOTOGRAPH

This new *pelargonium* plant is illustrated by the accompanying photograph which shows flowers and foliage of the plant. The colors shown are as true as can be reasonably obtained by conventional photographic procedures. The photograph is of a 6-month old plant taken in October 2009 grown from a rooted cutting in a 12 centimeter pot in a glass greenhouse in Stuttgart, Germany under conditions which approximate those generally used in normal horticultural practice.

DESCRIPTION OF THE NEW VARIETY

The following detailed descriptions set forth the distinctive characteristics of 'KLEPZ11276'. The data which define these characteristics were collected from asexual reproductions carried out in Stuttgart, Germany. The plant history was taken on 3-month old, un-pinched plants grown in 12 centimeter pots in a glass greenhouse in Stuttgart, Germany. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family*.—Geraniaceae.
- *Species*.—*Pelargonium zonale*.
- *Common name*.—*Pelargonium* (Geranium).
- *Denomination*.—'KLEPZ11276'.

Parentage:
- *Female parent*.—Geranium named 'KLEGANY' (U.S. Plant Pat. No. 9,110).
- *Male parent*.—*Pelargonium* plant named 'P 1101' (unpatented).

Plant:
- *Habit*.—Strong and upright.
- *Height to the top of the umbels*.—25.0 cm to 35.0 cm.
- *Spread*.—28.0 cm.
- *Life cycle*.—Spring to autumn.
- *Form*.—Round, bushy.
- *Time to produce a rooted cutting*.—18 days.
- *Time to bloom from propagation*.—Approximately 84 days.
- *Lastingness of inflorescence on the plant*.—12 days.

Stems:
- *Stem color*.—RHS 137D.
- *Pubescence*.—Present, very short.
- *Pubescence color*.—RHS 155C.
- *Stem form*.—Upright, erect.
- *Diameter*.—0.6 cm to 1.0 cm.
- *Length*.—4.0 cm to 10.0 cm.
- *Internode length*.—0.5 cm to 1.5 cm.

Leaves:
- *Arrangement*.—Alternate.
- *Shape*.—Round.
- *Apex*.—Round.
- *Base*.—Open.
- *Margin*.—Crenate.
- *Surface texture* (*both surfaces*).—Dull.
- *Length*.—5.0 cm to 6.0 cm.
- *Width*.—6.0 cm to 7.0 cm.
- *Color*.—Upper surface: RHS 137A. Lower surface: RHS 137C.
- *Fragrance*.—Absent.
- *Surface pubescence*.—Present, very short.
- *Surface pubescence color*.—RHS 155C.
- *Petiole*.—Length: 6.0 cm to 8.0 cm. Diameter: 0.15 cm. Color: RHS 137C.
- *Venation pattern*.—Palmate.
- *Venation color* (*both surfaces*).—RHS 137D.
- *Zonation*.—Width: 1.2 cm to 1.5 cm. Location: In the middle of the leaves. Color: RHS 200C (young leaves); RHS 147A (older leaves).

Inflorescence:
- *Flowering habit*.—Continuous.
- *Umbels*.—Length: 12.0 cm. Diameter: 14.0 cm.
- *Individual florets of the umbel*.—Depth: 2.0 cm. Diameter: 3.0 cm to 4.0 cm.
- *Flowers per umbel*.—4.
- *Umbels per plant*.—4.
- *Fragrance*.—Absent.

Flower buds:
- *Cluster shape*.—Round.
- *Cluster size*.—Length: 2.0 cm to 4.0 cm. Width: 2.0 cm to 4.0 cm. Buds per cluster: 12 to 25.
- *Bud*.—Length: 0.6 cm to 0.8 cm. Diameter: 0.3 cm to 0.6 cm. Shape: Ovate. Apex: Acute. Base: Obtuse. Margin: Plane. Color: RHS 137B.

Petals:
- *Quantity per flower*.—6 to 8.
- *Shape*.—Spatulate.
- *Apex*.—Round, entire.
- *Base*.—Obtuse.
- *Margin*.—Entire.
- *Length*.—2.5 cm.
- *Width*.—2.0 cm.
- *Texture* (*both surfaces*).—Smooth.
- *Color of lobes*.—Upper lobes: Upper surface: RHS N66A with RHS N34B in center. Lower surface: RHS N66B. Lower lobes: Upper surface: RHS 67B. Lower surface: RHS N67C.

Sepals:
- *Quantity per flower*.—5.
- *Shape*.—Elliptic.
- *Apex*.—Acute.
- *Base*.—Obtuse.
- *Margin*.—Entire.
- *Color*.—Upper surface: RHS 137C. Lower surface: RHS 137C and RHS 137D.
- *Length*.—0.5 cm to 2.0 cm.
- *Width*.—0.4 cm.

Pedicel:
- *Length*.—1.5 cm.
- *Diameter*.—0.6 cm.
- *Color*.—RHS 137D.
- *Texture*.—Slightly rough.

Peduncle:
- *Length*.—12.0 cm to 15.0 cm.
- *Diameter*.—0.4 cm to 0.6 cm.
- *Color*.—RHS 137C.
- *Texture*.—Slightly rough.

Reproductive organs:
- *Stamens*.—Quantity per flower: Moderate. Anther length: 0.4 cm. Filament length: 0.6 cm. Filament color: RHS 155D. Pollen amount: Moderate. Pollen color: RHS 41C.
- *Pistils*.—Quantity per flower: 1. Stigma color: RHS 73C. Style length: 0.4 cm. Style color: RHS 155D. Ovary arrangement: Single, upright. Ovary color: RHS 140D.

Fruit and seed set: None observed.

Disease, pest, and stress resistance: No particular resistance observed.

COMPARISON WITH PARENTAL AND COMMERCIAL VARIETIES

'KLEPZ11276' differs from the female parent 'KLEGANY' (U.S. Plant Pat. No. 9,110) in that 'KLEPZ11276' has a medium strong growth habit, red-purple flowers with orange centers, and medium green leaves with zonation, whereas 'KLEGANY' has a stronger growth habit, pink flowers with an eye, and light green leaves without zonation.

'KLEPZ11276' differs from the male parent 'P 1101' (unpatented) in that 'KLEPZ11276' has red-purple flowers with orange centers and medium green leaves with zonation, whereas 'P 1101' has purple flowers with an eye and light green leaves without zonation.

'KLEPZ11276' differs from the commercial variety 'Arcona 2000' (unpatented) in that 'KLEPZ11276' has a strong growth habit, red-purple flowers with orange centers, and leaves with zonation, whereas 'Arcona 2000' has a medium growth habit, purple-red flowers, and leaves with weak zonation.

We claim:

1. A new and distinct variety of *pelargonium* plant named 'KLEPZ11276' as shown and described herein.

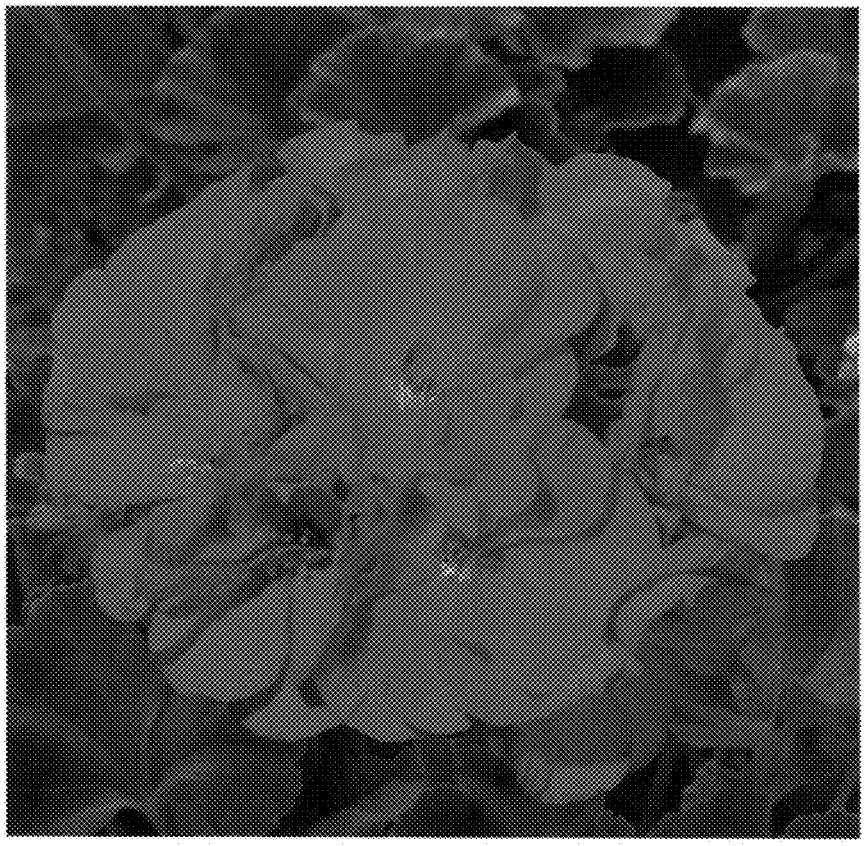

* * * * *